United States Patent
Okano et al.

(10) Patent No.: US 9,127,270 B2
(45) Date of Patent: Sep. 8, 2015

(54) CELL PATTERN RECOVERY TOOL

(75) Inventors: Teruo Okano, Ichikawa (JP); Masayuki Yamato, Tokyo (JP); Tatsuya Shimizu, Hachioji (JP); Masatoshi Kuroda, Kashiwa (JP)

(73) Assignees: TOKYO WOMEN'S MEDICAL UNIVERSITY, Tokyo (JP); DAI NIPPON PRINTING CO., LTD., Tokyo (JP)

( * ) Notice: Subject to any disclaimer, the term of this patent is extended or adjusted under 35 U.S.C. 154(b) by 495 days.

(21) Appl. No.: 13/125,491

(22) PCT Filed: Aug. 11, 2009

(86) PCT No.: PCT/JP2009/064374
§ 371 (c)(1),
(2), (4) Date: May 10, 2011

(87) PCT Pub. No.: WO2010/047171
PCT Pub. Date: Apr. 29, 2010

(65) Prior Publication Data
US 2011/0207220 A1    Aug. 25, 2011

(30) Foreign Application Priority Data
Oct. 22, 2008    (JP) .................................. 2008-271850

(51) Int. Cl.
*C12N 5/071* (2010.01)
*C12N 11/02* (2006.01)
*C12N 5/00* (2006.01)

(52) U.S. Cl.
CPC .............. *C12N 11/02* (2013.01); *C12N 5/0062* (2013.01); *C12N 2535/10* (2013.01); *C12N 2539/10* (2013.01)

(58) Field of Classification Search
CPC .. C12N 2539/10; C12N 11/02; C12N 5/0062; C12N 2535/10; C12N 5/0068; C12N 2533/30; C08J 7/042; C08J 2467/00; C09J 167/00
See application file for complete search history.

(56) References Cited

U.S. PATENT DOCUMENTS

| 4,551,485 A | 11/1985 | Ragan et al. |
| 2004/0197907 A1 | 10/2004 | Kataoka et al. |

(Continued)

FOREIGN PATENT DOCUMENTS

| EP | 0 382 214 A1 | 8/1990 |
| EP | 1 859 817 A1 | 11/2007 |

(Continued)

OTHER PUBLICATIONS

Webpage from http://www.chrtape.com/uploadedFiles/sgchrtape/Documents/CHRTape-Film-Mseries-1Mil-AFF1135.pdf, accessed May 29, 2013, attached as NPL pdf titled "PET tape".*

(Continued)

*Primary Examiner* — Ralph Gitomer
*Assistant Examiner* — Trent Clarke
(74) *Attorney, Agent, or Firm* — Oliff PLC

(57) ABSTRACT

This invention provides a cell pattern recovery tool comprising a base material layer having a surface subjected to easy adhesion treatment, a temperature responsive polymer layer that is provided on the base material layer and has a surface subjected to silane treatment, and a cell adhesion inhibiting material layer provided on the temperature responsive polymer layer. According to the present invention, a cell pattern can be rapidly recovered while maintaining the cell pattern stably and reliably under minimally invasive conditions for the cells.

11 Claims, 3 Drawing Sheets

(56) References Cited

U.S. PATENT DOCUMENTS

| | | | |
|---|---|---|---|
| 2006/0240552 A1* | 10/2006 | Yamato et al. | 435/368 |
| 2007/0015277 A1* | 1/2007 | Hattori et al. | 435/325 |
| 2007/0259328 A1 | 11/2007 | Morita et al. | |
| 2007/0274968 A1 | 11/2007 | Hattori et al. | |
| 2008/0124795 A1 | 5/2008 | Miyake et al. | |
| 2008/0131476 A1 | 6/2008 | Kanzaki et al. | |
| 2008/0227203 A1 | 9/2008 | Watanabe et al. | |
| 2009/0011504 A1 | 1/2009 | Kataoka et al. | |

FOREIGN PATENT DOCUMENTS

| | | |
|---|---|---|
| JP | A-05-192130 | 8/1993 |
| JP | B2-06-104061 | 12/1994 |
| JP | A-2003-082119 | 3/2003 |
| JP | A-2005-342112 | 12/2005 |
| JP | A-2006-008975 | 1/2006 |
| JP | A-2007-312736 | 12/2007 |
| JP | A-2008-220320 | 9/2008 |
| WO | WO 03/010302 A1 | 2/2003 |
| WO | WO 2005/085413 A1 | 9/2005 |
| WO | WO 2006/093153 A1 | 9/2006 |

OTHER PUBLICATIONS

Kazuyoshi Itoga, Masayuki Yamato, Jun Kobayashi, Akihiko Kikuchi, Teruo Okano, Cell micropatterning using photopolymerization with a liquid crystal device commercial projector, 2004, Biomaterials, vol. 25, pp. 2047-2053.*

X.-Z Zhang, R.-X. Zhuo, Synthesis and characterization of a novel thermosensitive gel with fast response, 1999, Colloid Polym Sci, vol. 277, pp. 1079-1082.*

International Preliminary Report on Patentability issued in International Patent Application No. PCT/JP2009/064374 dated May 17, 2011.

Itoga et al., "Cell sheet engineering—Fabrication and utilization of patterned cell sheet—," *Japanese Journal of Clinical Medicine*, 2008, vol., 66, No. 5, pp. 887-891 (with Abstract).

Fukumori et al., "Observation of cell detachment behavior from temperature responsive polymer grafted surfaces using total internal reflection fluorescence microscopy," *Polymer Preprints*, Japan, 2006, vol. 55, No. 2, pp. 4494-4495 (with Abstract).

Fukumori et al., "Control of cell detachment on poly($N$-isopropylacrylamide) grafted glass sufaces using electron beam irradiation," *Polymer Preprints*, Japan, 2005, vol. 54, No. 2, pp. 5221-5222 (with Abstract).

International Search Report issued in International Patent Application No. PCT/JP2009/064374 dated Nov. 17, 2009.

Japanese Patent Office, Notification of Reason for Rejection issued on Sep. 6, 2013 in Japanese Patent Application No. 2008-271850 w/English-language Translation.

Dec. 3, 2013 Notification of Reason for Rejection issued in Japanese Patent Application No. 2008-271850 (with English-language translation).

Tsuda Y., et al., "The use of patterned dual thermoresponsive surfaces for the collective recovery as co-cultured cell sheets", Biomaterials, vol. 26, No. 14, May 1, 2005, pp. 1885-1893.

Dec. 18, 2012 Supplementary European Search Report issued in EP 09 82 1871.

* cited by examiner

CELL PATTERN RECOVERY TOOL

CROSS-REFERENCE TO RELATED APPLICATION

This application is based upon and claims the benefit of priority from the prior Japanese Patent Applications No. 271850/2008, filed on Oct. 22, 2008; the entire disclosures of which are incorporated herein by reference.

BACKGROUND OF THE INVENTION

1. Field of Invention

The present invention relates to a novel cell pattern recovery tool (or a cell cultivation support for cell pattern recovery). More specifically, the present invention relates to a cell pattern recovery tool that can cultivate cells so as to have a desired cell shape to form a cell pattern (sheet) that can be rapidly recovered. Further, the present invention relates to a process for producing the cell pattern recovery tool and a process for preparing a cell pattern using the cell pattern recovery tool.

2. Background Art

A cell sheet is a sheet-like cell aggregate comprising cells that have been linked to one another through at least a single layer by cell junction. The cell pattern is a cell sheet that has been formed so as to have a desired specific shape. The cell sheet and the cell pattern are often used, for example, for regenerative medical techniques.

The cell sheet is obtained by cell cultivation on a support such as a petri dish. The cell sheet formed on the support is strongly bound to the surface of the support, for example, through adhesive molecules. Accordingly, rapidly separating the cell sheet from the cultivation support without breaking binding between cells is not easy. Accordingly, in the case of a cell pattern, due to a specific shape, further difficulties are encountered in rapidly, stably, and reliably separating the cell pattern from the cultivation support.

Up to now, various studies have been made to propose methods that can efficiently separate a cell sheet from a cell cultivation support. Conventional separating methods are classified roughly into two groups. The methods belonging to the first group are to weaken binding between the support and the cells by an enzymatic reaction. The methods belonging to the second group are to use a support having low cell adherence or a support with adherence of cells thereto being variable.

More specifically, the methods belonging to the first group comprise degrading proteins constituting intercellular adhesion molecules (tight junction, adhering junction, desmosome junction, gap junction, or hemidesmosome junction), collagen connective tissues surrounding a culture, and extracellular matrix (ECM) formed between cells and the support by enzymes such as proteases (proteolytic enzymes) and collagenases (collagenolytic enzymes). These methods, however, weaken junction between cells and the surface of the support, as well as junction between cells. Accordingly, the methods belonging to the first group cause not a little damage to the cell sheet. The binding substances degraded by this method are substances produced in cells which are cultivated, tissues, and organs. Accordingly, even after the separation, binding substances that have been degraded under given conditions and in a given period can be regenerated. The regeneration of the binding substances, however, takes a lot of time.

Regarding a method using a support with adherence of cells thereto being variable among the methods belonging to the second group, for example, Japanese Patent Publication No. 104061/1994 (EP 0382214A) (document 1) discloses a support having a cell growth surface covered with a temperature responsive polymer. This document describes a process for producing a temperature responsive polymer layer by a graft polymerization method in which electron beam is applied to cause both a monomer polymerization reaction and a (grafting) reaction by which at least one end of a temperature responsive polymer is covalently bonded to molecules constituting a base material and thus to immobilize the temperature responsive polymer to the surface of the base material. Further, for example, Japanese Patent Application Laid-Open Publication No. 192130/1993 (document 2) also refers to the use of a temperature responsive polymer in cell cultivation. In these documents, however, no study has been made to rapidly and stably recover a cell pattern in the cultivation support using a temperature responsive polymer.

Japanese Patent Application Laid-Open Publication No. 082119/2003 (document 3) discloses a cell recovery membrane and a process for producing the cell recovery membrane. Further, Japanese Patent Application Laid-Open Publication No. 342112/2005 (US 2007259328A) (document 4) discloses a tissue body which has been formed in vitro and recovered in such a state that a cell pattern is maintained, and a process for producing the tissue body. Japanese Patent Application Laid-Open Publication No. 8975/2006 (document 5) discloses the cultivation of desired cells according to a desired pattern. These documents, however, do not describe that a temperature responsive polymer layer is provided and a cell adhesion inhibiting material layer is formed, on the temperature responsive polymer layer, in a desired cell pattern shape. Accordingly, these documents neither describe nor suggest the formation of a cell pattern which is then rapidly recovered. In the method disclosed in patent document 5, ultraviolet irradiation is also performed for cell pattern separation.

Therefore, a cultivation support, that is, a cell pattern recovery tool, that can rapidly recover a cell pattern while maintaining the cell pattern stably and reliably under minimally invasive conditions for the cells has been still demanded.

SUMMARY OF THE INVENTION

The present inventors have now found that, when a temperature responsive polymer is grafted in a nanoscale thickness on a polyethylene terephthalate (PET) film which is a base material having a surface subjected to easy adhesion treatment, and, further, a cell adhesion inhibiting material is immobilized in a microscale thickness on the temperature responsive polymer layer, seeded cells can be cultivated under conventional cultivation conditions to form a cell pattern on the layer structure formed on the base material, and, further, the cell pattern can be rapidly recovered in 20 min or less on an organic thin film, when the organic thin film is attached to the structure, by lowering the temperature of the structure to room temperature which is below the critical dissolution temperature at which the temperature responsive polymer is converted from a hydrophobic state to a hydrophilic state. Further, the present inventors have found that, in immobilizing a cell adhesion inhibiting material on the temperature responsive polymer layer, silane treatment of the temperature responsive polymer layer can realize the immobilization of the cell adhesion inhibiting material under mild conditions without causing the temperature response of the temperature responsive polymer to disappear in an efficient and reliable manner. The present invention has been made based on such finding.

An object of the present invention is to provide a cell pattern recovery tool that can rapidly recover a cell pattern while maintaining the cell pattern stably and reliably under minimally invasive conditions for the cells.

According to the present invention, there is provided a cell pattern recovery tool comprising:

a base material layer having a surface subjected to easy adhesion treatment;

a temperature responsive polymer layer that is provided on the base material layer and has a surface subjected to silane treatment; and a cell adhesion inhibiting material layer provided on the temperature responsive polymer layer.

According to one preferred embodiment of the present invention, in the cell pattern recovery tool according to the present invention, a contemplated cell pattern is formed by, in the cell adhesion inhibiting material layer, alternately disposing areas where the temperature responsive polymer layer is exposed (cell adhesion areas) and areas where the temperature responsive polymer layer is covered with the cell adhesion inhibiting material (cell adhesion inhibiting areas).

According to another one preferred embodiment of the present invention, in the cell pattern recovery tool according to the present invention, the width of the areas which are located between the areas, where the temperature responsive polymer layer is exposed, and is covered with a cell adhesion inhibiting material is 1 μm to 500 μm.

According to a preferred embodiment of the present invention, in the cell pattern recovery tool according to the present invention, the cell adhesion inhibiting material is an ethylene glycol material.

According to another preferred embodiment of the present invention, in the cell pattern recovery tool according to the present invention, the silane treatment of the temperature responsive polymer layer is carried out by coating the temperature responsive polymer layer with methacryloxysilane.

According to a further preferred embodiment of the present invention, in the cell pattern recovery tool according to the present invention, the temperature responsive polymer constituting the temperature responsive polymer layer is a poly-N-isopropylacrylamide (PIPAAm).

According to a more preferred embodiment of the present invention, the cell pattern recovery tool according to the present invention further comprises a polystyrene dish provided with the base material layer at its bottom through a pressure-sensitive adhesive layer.

According to another aspect of the present invention, there is provided a process for preparing a cell pattern recovery tool, the process comprising:

forming a temperature responsive polymer layer on base material layer having a surface subjected to easy adhesion treatment; then subjecting the surface of the temperature responsive polymer layer to silane treatment; and forming a cell adhesion inhibiting material layer, through a photopolymerization reaction on the silane-treated surface, in a shape that can form a contemplated cell pattern.

Further, according to a further aspect of the present invention, there is provided a process for preparing a cell pattern, the process comprising: seeding cells on a cell pattern recovery tool according to the present invention; cultivating the cells under temperature conditions suitable for cultivation; then bringing the tool to a critical dissolution temperature, at which the temperature responsive polymer is converted from a hydrophobic state to a hydrophilic state, or below to separate the cells from the tool, whereby a contemplated cell pattern is rapidly recovered. In this case, preferably, the critical dissolution temperature is room temperature.

The cell pattern according to the present invention has been prepared by the process for preparing a cell pattern according to the present invention.

The cell pattern recovery tool according to the present invention is advantageous in that a desired cell pattern is formed on the tool by cell cultivation, and the cell pattern can be rapidly recovered while maintaining the cell pattern stably and reliably under minimally invasive conditions for the cells. According to the present invention, a desired cell pattern can be transferred onto an organic thin film, which is attached to the surface of the tool, by merely changing the temperature of the tool, in which cells are being cultivated, from a conventional animal cell cultivation temperature to room temperature, and the cell pattern can be recovered at high rapidness (for example, in 20 min or less) unattainable by the prior art technique. Since the cell pattern can be rapidly recovered, the tool can be used for processes suitable for the mass production of cell patterns. Further, the cell pattern recovered by the cell pattern recovery tool according to the present invention has a desired shape. At the same time, adhesion factors present on the surface thereof remain intact. Therefore, the cell pattern recovery tool can be advantageously utilized for practice of regenerative medical techniques and researches for the regenerative medical techniques.

DETAILED DESCRIPTION OF THE INVENTION

Cell Pattern Recovery Tool

As described above, the cell pattern recovery tool according to the present invention basically comprises:

a base material layer having a surface subjected to easy adhesion treatment;

a temperature responsive polymer layer that is provided on the base material layer and has a surface subjected to silane treatment; and a cell adhesion inhibiting material layer provided on the temperature responsive polymer layer. That is, the cell pattern recovery tool according to the present invention comprises at least the base material layer, the temperature responsive polymer layer, and the cell adhesion inhibiting material layer. If necessary, the cell pattern recovery tool may further comprise a polystyrene dish provided at the bottom of the polystyrene dish, for example, through a pressure-sensitive adhesive layer.

Figure 1:
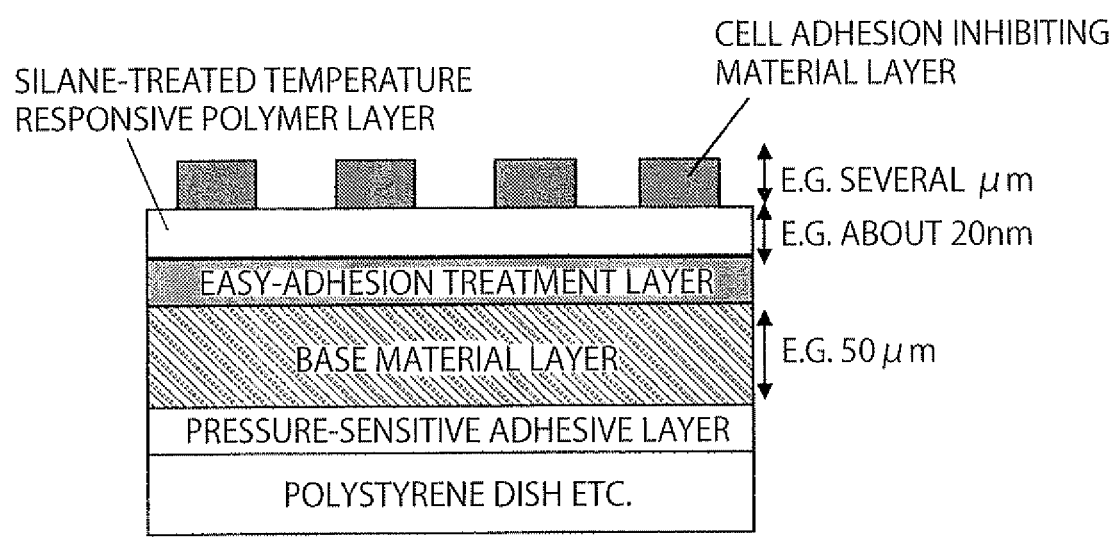
FIG. 1 is a conceptual diagram of a cell pattern recovery tool according to the present invention. In the drawing, the layer thickness is an example.

FIG. 1 is a conceptual diagram of a cell pattern recovery tool according to the present invention.

The cell pattern recovery tool means a support for cell cultivation (or a base material or a device for cell cultivation) that can cultivate cells on the tool and, at the same time, can prepare and rapidly recover a cell pattern (a cell sheet) having a desired shape usable for practice of regenerative medical techniques.

Base Material Layer

The base material for the "base material layer" in the "base material layer having a surface subjected to easy adhesion treatment" may be any material as long as the surface of the material can be subjected to easy adhesion treatment which will be described later. Examples thereof include polyethylene terephthalates (PETs), polystyrenes (PSs), polycarbonates (PCs), TACs (triacetylcelluloses), polyimides (PIs), nylons (Nys), low-density polyethylenes (LDPEs), medium-density polyethylenes (MDPEs), vinyl chlorides, vinylidene chlorides, polyphenylene sulfides, polyethersulfones, polyethylene naphthalates, polypropylenes, or acrylic resins. Biodegradable polymers such as polylactic acids, polyglycolic acids, polycaprolactones, or copolymers thereof may also be usable as the base material. Preferred are polyethylene terephthalates, polystyrenes, and polycarbonates. More preferred is polyethylene terephthalates. Among them, polyethylene terephthalate particularly possesses excellent properties such as excellent transparency, dimensional stability, mechanical properties, electrical properties, and chemical resistance and thus is suitable as materials for the cell pattern recovery tool.

In the "base material layer having a surface subjected to easy adhesion treatment," the expression "surface subjected to easy adhesion treatment" with respect to the base material may be, for example, the surface, of the base material, on which an easy adhesion layer has been formed with an easy adhesion agent such as a polyester, an acrylic ester, polyurethane, polyethyleneimine, a silane coupling agent, or perfluorooctanesulfonic acid (PFOS). Among the easy adhesion agents listed above, preferred easy adhesion agents include polyesters, acrylic esters, and polyurethanes. When the surface of the base material is subjected to the easy adhesion treatment, the temperature responsive polymer layer can easily be bonded to the surface of the base material to cover the surface of the base material.

The "easy adhesion treatment of the surface" of the base material will be described by taking, as a specific example, the case where the base material is polyethylene terephthalate. The easy adhesion can be imparted to the polyethylene terephthalate film by coating an easy adhesion-imparting coating material by an in-line coating method or an off-line coating method. A combination of the easy adhesion agent, for example, with a melamine resin as a crosslinking agent component can be mentioned as an example of the easy adhesion-imparting coating material. The in-line coating method is a method in which the coating material is coated in the step of forming a film. On the other hand, the off-line coating method is a method in which the coating material is coated by a coater onto a biaxially stretched polyethylene terephthalate film, formed by film formation, to form a coating which is then dried. The coating material may be coated by any coating method. Examples of coating methods include roll coating, gravure coating, micro gravure coating, reverse coating, reverse gravure coating, bar coating, roll brush coating, air knife coating, curtain coating, and die coating. These coating methods may be properly used solely or in a combination of two or more.

The thickness of the base material layer having a surface subjected to easy adhesion treatment is not particularly limited and may be, for example, 10 to 500 µm, preferably 50 to 200 µm.

The base material layer having a surface subjected to easy adhesion treatment may if necessary be a commercially available product.

Temperature Responsive Polymer Layer

In the present invention, as described above, the "temperature responsive polymer layer having a surface subjected to silane treatment" is provided on a surface of the base material layer, particularly the base material layer subjected to easy adhesion treatment.

The temperature responsive polymer usable in the "temperature responsive polymer layer" can be rendered hydrophobic under a cell cultivation temperature (generally about 37° C.) and can be rendered hydrophilic under a temperature at which the cell sheet after cultivation is recovered.

The temperature at which the temperature responsive polymer is changed from a hydrophobic state to a hydrophilic state (i.e., a critical dissolution temperature (T) in water) is not particularly limited. From the viewpoint of easiness in recovering the cell sheet after cultivation, however, the critical dissolution temperature is preferably below the cell cultivation temperature. When the temperature responsive polymer component is contained, scaffold of cells (a cell adhesion surface) can be satisfactorily ensured during cell cultivation and, thus, the cells can be efficiently cultivated, while, when the cell sheet after cultivation is recovered, the cell sheet can be more easily recovered by changing the hydrophobic part to a hydrophilic state and separating the cell sheet after cultivation from the cell cultivation base material. A temperature responsive polymer which is hydrophilic at a temperature below a predetermined critical dissolution temperature and is hydrophobic at a temperature at or above the critical dissolution temperature is particularly preferred. The critical dissolution temperature of the temperature responsive polymer particularly refers to a lower critical dissolution temperature.

The temperature responsive polymer preferably usable in the present invention specifically has a lower critical dissolution temperature T of 0 to 80° C., preferably 0 to 50° C., more preferably approximately room temperature. When T is above 80° C., disadvantageously, the cells are possibly killed. On the other hand, when T is below 0° C., in general, disadvantageously, the cell growth rate is extremely lowered, or otherwise the cells are, killed. For example, when T is approximately room temperature, the temperature of the temperature responsive polymer can be lowered to the temperature T from the cell cultivation temperature (generally approximately 37° C.) by simply taking the tool during cultivation from a cultivation incubator. Accordingly, the operability can be further improved.

Such suitable polymers include acrylic polymers or methacrylic polymers and are also described, for example, in patent document 1. Specific suitable polymers include, for example, poly-N-isopropylacrylamide (T=32° C.), poly-N-n-propylacrylamide (T=21° C.), poly-N-n-propylmethacrylamide (T 32° C.), poly-N-ethoxyethylacrylamide (T=about 35° C.), poly-N-tetrahydrofurfurylacrylamide (T=about 28° C.), poly-N-tetrahydrofurfurylmethacrylamide (T=about 35° C.), and poly-N,N-diethylacrylamide (T=32° C.). Other polymers include, for example, poly-N-ethylacrylamide, poly-N-isopropylmethacrylamide, poly-N-cyclopropylacrylamide, and poly-N-cyclopropylmethacrylamide; poly-N-acryloylpyrrolidine; poly-N-acryloylpiperidine; polymethyl vinyl ether; alkyl substituted cellulose derivatives such as methyl cellulose, ethyl cellulose, and hydroxypropyl cellulose; polyalkylene oxide block copolymers typified, for example, by block copolymers of polypropylene oxide with polyethylene oxide; and polyalkylecy oxide block copolymers.

In a preferred embodiment of the present invention, the polymer is poly-N-isopropylacrylamide (PIPAAm), poly-N- n-propylmethacrylamide, or poly-N,N-diethylacrylamide, more preferably poly-N-isopropylacrylamide.

Monomers for the formation of these polymers are, for example, monomers that provide homopolymers having T=0 to 80° C. and are polymerizable by radiation irradiation (preferably electron beam irradiation). Monomers include, for example, (meth)acrylamide compounds, N-(or N,N-di)alkyl substituted (meth)acrylamide derivatives, cyclic group-containing (meth)acrylamide derivatives, and vinyl ether derivatives. These monomers may be used solely or in a combination of two or more. When only one type of monomer is used, a homopolymer is formed on the base material. On the other hand, when a plurality of types of monomers are used together, a copolymer is formed on the base material. Both the cases are included in the present invention. For example, when "T" should be regulated depending upon the type of growing cells, or when the interaction between the covering material and the cell cultivation support should be enhanced, or when the hydrophilic/hydrophobic balance of the cell support should be regulated, monomers other than described above may be added for copolymerization. Further, a graft or block copolymer of the above polymer, used in the present invention, with other polymer or a mixture of the polymer according to the present invention with other polymer may also be used. Further, crosslinking is also possible as long as the properties inherent in the polymer are not sacrificed.

In a preferred embodiment of the present invention, the monomer is N-isopropylacrylamide, N-n-propylmethacrylamide, or N,N-diethylacrylamide, more preferably N-isopropylacrylamide.

In the present invention, the temperature responsive polymer layer may be formed as follows.

Specifically, the temperature responsive polymer layer may be formed by preparing a coating composition containing the monomer and an organic solvent that can dissolve the monomer, and coating the coating composition by a conventional coating method. Conventional coating methods when the coating composition is coated onto a base material layer having a small area include, for example, coating, for example, by a spin coater or a bar coater, and spray coating. Conventional coating methods when the coating composition is coated onto a base material layer having a large area include, for example, blade coating, gravure coating, rod coating, knife coating, reverse roll coating, and offset gravure coating.

The organic solvent that can dissolve the monomer is not particularly limited as long as the organic solvent can dissolve the monomer. Preferably, the organic solvent has a boiling point of 120° C. or below, particularly 60 to 110° C., under atmospheric pressure. Specific preferred solvents include methanol, ethanol, n-propanol, 2-propanol, n-butanol, 2-butanol, and water. These solvents may be used in combination. Other solvents, for example, 1-pentanol, 2-ethyl-1-butanol, 2-butoxyethanol, and ethylene (or diethylene)glycol or its monoethyl ether are also usable. If necessary, for example, acids typified by sulfuric acid and the like and Mohr's salts may be incorporated as additives in the solution.

In more preferred embodiment of the present invention, the organic solvent that can dissolve the monomer is 2-propanol. The content of the monomer in the coating composition is preferably 5 to 70% by weight.

After the formation of a coating film by coating the coating composition, electron beams are applied to the coating film to cause the formation of a polymer by a polymerization reaction and a grafting reaction between the surface of the base material and the polymer, and, if necessary, the coating film is dried to remove the organic solvent.

The temperature responsive polymer layer thus formed may if necessary be further washed. Washing is preferred for the reason that not only polymer molecules immobilized by a covalent bond but also free polymer molecules remaining unimmobilized, a monomer(s) remaining unreacted and the like are considered to be present on the surface of the base material and the free polymer and unreacted compound can be removed by washing. Further, washing is also advantageous in enhancing the effectiveness of silane treatment which will be described later. The method for washing is not particularly limited. Typical methods for washing include immersion washing, swinging washing, shower washing, spray washing, and ultrasonic cleaning. Typical washing liquids include various aqueous, alcoholic, hydrocarbon, chlorinated hydrocarbon, and acid/alkali washing liquids.

In the present invention, the coverage of the temperature responsive polymer layer may be a coating weight necessary for the grafted polymer to exhibit temperature responsive properties. The coverage is, for example, 5 to 80 $\mu g/cm^2$, preferably 10 to 50 $\mu g/cm^2$. When the coverage of the polymer exceeds 50 $\mu g/cm^2$, the cell adhesion is disadvantageously lowered. On the other hand, when the coverage of the polymer is less than 5 $\mu g/cm^2$, the separability of the cells is lowered.

In the present invention, the surface of the temperature responsive polymer layer thus formed is subjected to silane treatment, for example, with a conventional silane coupling agent, for example, methacryloxysilane, vinylsilane, aminosilane, or epoxysilane. Preferably, the silane coupling agent usable herein is methacryloxysilane. When the surface of the temperature responsive polymer layer has not been subjected to silane treatment, binding between the temperature responsive polymer layer and the cell adhesion inhibiting material layer is unsatisfactory. In this case, the formation of a cell adhesion inhibiting material layer in a cell pattern form on the temperature responsive polymer layer is not sometimes unsatisfactory. On the other hand, when the surface is subjected to silane treatment, reliable binding between the temperature responsive polymer layer and the cell adhesion inhibiting material layer can be realized and a desired cell pattern can be reliably formed by the cell adhesion inhibiting material layer.

The silane treatment can be carried out by dissolving a silane coupling agent in an organic solvent that can dissolve the silane coupling agent, and coating the solution onto a temperature responsive polymer layer formed, for example, by a conventional coating method, for example, spin coating, die coating, dip coating, gravure printing, or CVD (chemical vapor deposition). For example, when the solution is coated by spin coating, the spin coating can be carried out at 700 to 2000 rpm for approximately 3 to 20 seconds.

Organic solvents that can dissolve the silane coupling agent include, for example, isopropyl alcohol (IPA), ethanol, 1,3-butanediol, n-butanol, pentane, chlorobenzene, methyl alcohol, n-propyl alcohol, isopentyl alcohol, benzyl alcohol, phenol, diethyl ether, 1,4-dioxane, ethylene glycol dimethyl ether, diethylene glycol dimethyl ether, acetonitrile, propionitrile, methyl acetate, ethyl acetate, methylene chloride, 1,2-dichloroethane, nitroethane, nitromethane, nitrobenzene, aniline, pyridine, morpholine, quinoline, dimethylsulfoxide, N,N-dimethylformamide, N,N-dimethylacetamide, and water. These solvents may be used in combination. The organic solvent is preferably isopropyl alcohol.

It is considered that, in the temperature responsive polymer layer having a silane-treated surface, the silane-treated layer is integrated with the temperature responsive polymer or is not distinguishable from the temperature responsive polymer, that is, is not formed independently of the temperature responsive polymer layer. Accordingly, in the present specification, the temperature responsive polymer layer sometimes connotes a silane-treated temperature responsive polymer layer. These are theoretical or hypothetical and do not limit the present invention.

The coverage of the polymer or the coverage associated with silane treatment can be determined, for example, by fourier-transform infrared attenuated total reflection spectroscopy (an FT-IR-ATR method), by an analysis utilizing dyeing of the covered part or the uncovered part or dyeing with a fluorescent material, by a surface analysis utilizing contact angle measurement or the like, and by X-ray photoelectron spectroscopy (XPS), either solely or in an appropriate combination thereof.

In the cell pattern recovery tool according to the present invention, the thickness of the silane-treated temperature responsive polymer layer on a dry basis is preferably 0.001 to 10 µm, more preferably 0.01 to 0.03 µm.

Cell Adhesion Inhibiting Material Layer

In the present invention, as described above, the "cell adhesion inhibiting material layer" is formed on the silane-treated temperature responsive polymer layer.

Any material can be used as the cell adhesion inhibiting material without particular limitation as long as the material has cell adhesion inhibiting properties, that is, properties of inhibiting adhesion of cells to the material, and can form a cell adhesion inhibiting material layer by using a monomer for the cell adhesion inhibiting material together with a photopolymerization initiator and allowing a photopolymerization reaction to proceed in parts exposed to light (for example, ultraviolet light). Such cell adhesion inhibiting materials include, for example, polyethylene glycol resins, specifically water repellent materials such as polyethylene glycol diacrylates, polyethylene glycol methacrylates, phospholipid polymers, long-chain alkyl materials, fluorocarbon materials, and hydrophilic materials such as polyvinyl alcohols (PVAs).

Photopolymerization initiators usable herein include, for example, 2-hydroxy-4'-(2-hydroxyethoxy)-2-methylpropiophenone, camphoquinone, 1-hydroxycyclohexylphenylketone, 2,2-diethoxyacetophenone, 2-chlorobenzophenone, 2-ethylanthraquinone, 4,4'-bis(diethylamino) benzophenone, 9-fluorenone, benzil, benzoline, diphenyliodonium hexafluorophosphate, N-methyl-9-acridone, and tribromomethyl phenyl sulfone.

In the present invention, the cell adhesion inhibiting material layer can be formed as follows. Specifically, a solution containing the cell adhesion inhibiting material, the photopolymerization initiator, and a solvent that can dissolve these materials is prepared. The solution is coated by a conventional coating method. If necessary, the coating is masked in a desired cell pattern form, followed by the application of light (ultraviolet light) through mask irradiation to cause a photopolymerization reaction. Subsequently, the surface is washed with water or the like to wash away the areas not involved in the polymerization reaction, whereby a cell adhesion inhibiting material layer in a desired cell pattern form can be formed. Alternatively, a method may also be adopted in which a solution containing the cell adhesion inhibiting material, the photopolymerization initiator, and a solvent that can dissolve these materials is printed, for example, by ink jet printing, offset printing, gravure printing, flexographic printing, gravure offset printing, or screen printing to form a predetermined pattern, and whole surface light (ultraviolet light or light with an absorption wavelength of the photopolymerizaton initiator) is applied.

In the present invention, light, for example, with a wavelength of 150 to 600 nm may be applied as irradiation light at an illuminance of 1 to 100 mW/cm$^2$. Ultraviolet light is preferred.

According to a preferred embodiment of the present invention, in the cell adhesion inhibiting material layer, areas where the temperature responsive polymer layer is exposed and areas where the temperature responsive polymer layer is covered with the cell adhesion inhibiting material are alternately arranged to provide a contemplated cell pattern. That is, in the cell adhesion inhibiting material layer, a desired shape that can form a contemplated cell pattern (a cell sheet) is formed by alternately arranging the two types of areas. In this case, more preferably, the width of the area which is located between the areas, where the temperature responsive polymer layer is exposed, and is covered with a cell adhesion inhibiting material is 1 µm to 500 µm, still more preferably 2 to 200

In the cell pattern recovery tool according to the present invention, the thickness of the cell adhesion inhibiting material layer on a dry basis is preferably 0.01 to 15 µm, more preferably 0.05 to 1.5 µm.

Other Layer or Structure

In the present invention, the base material layer may be, for example, in a dish or film form. When a film-like base material is used, after the formation of a temperature responsive polymer layer grafted on a surface of the film-like base material, the structure can be fabricated into a shape (for example, a dish shape) suitable for cell cultivation. In the fabrication, if necessary, a member formed of other material can be used in combination with the base material. For example, a polystyrene dish or a petri dish is provided on the bottom of the base material layer through a pressure-sensitive adhesive layer. The assembly including the polystyrene dish or the petri dish may also be used as the cell pattern recovery tool according to the present invention.

Process for Producing Cell Pattern Recovery Tool

According to another aspect of the present invention, there is provided a process for producing a cell pattern recovery tool, the process comprising:

forming a temperature responsive polymer layer on a base material layer having a surface subjected to easy adhesion treatment; then subjecting the surface of the temperature responsive polymer layer to silane treatment; and forming a cell adhesion inhibiting material layer, through a photopolymerization reaction on the silane-treated surface, in a shape that can form a contemplated cell pattern.

Figure 2:
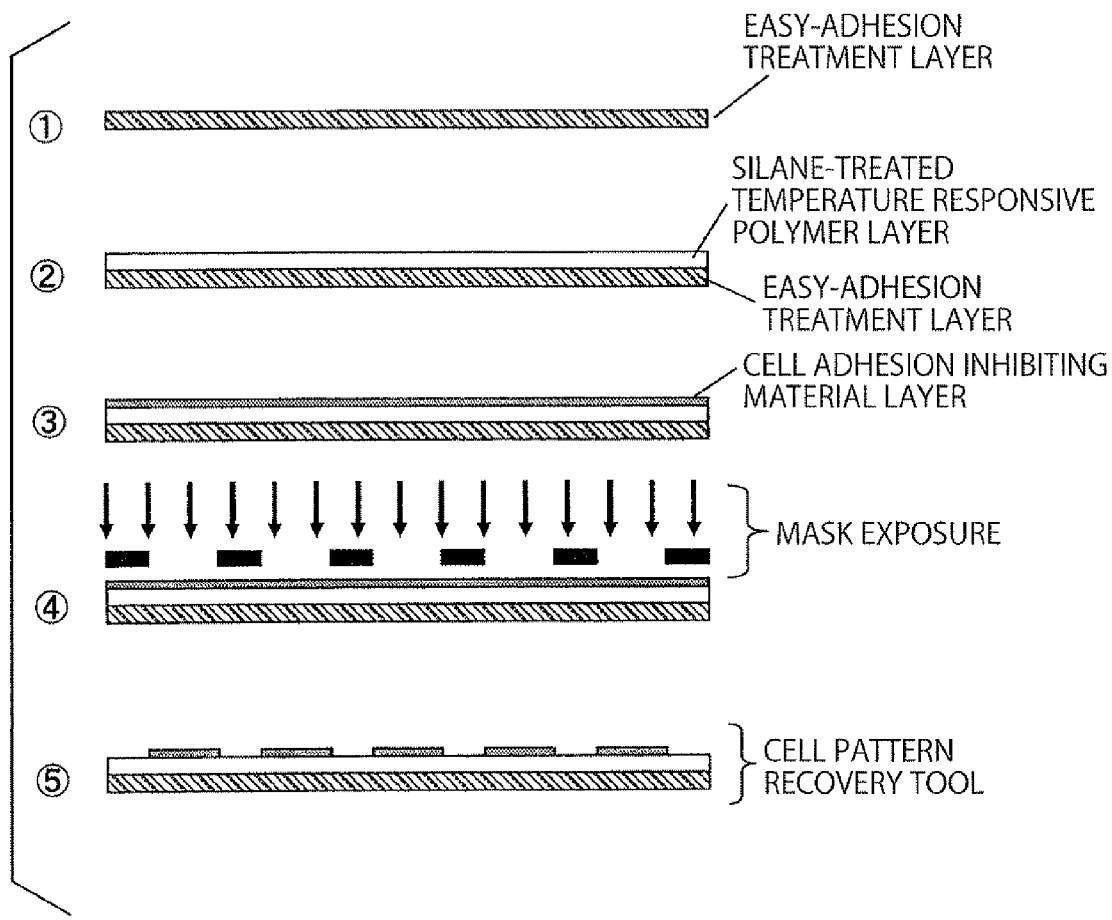
FIG. 2 is a conceptual diagram showing a production process of a cell pattern recovery tool according to the present invention. In the drawing, the steps of an example of the production process of a cell pattern recovery tool according to the present invention are successively shown from the top to the bottom of the drawing.

FIG. 2 is a conceptual diagram showing a specific embodiment of a process for producing a cell pattern recovery tool according to the present invention.

Process for Preparing Cell Pattern

As described above, the process for preparing a cell pattern according to the present invention comprises: seeding cells on a cell pattern recovery tool according to the present invention; cultivating the cells under temperature conditions suitable for cultivation; then bringing the tool to a critical dissolution temperature, at which the temperature responsive polymer is converted from a hydrophobic state to a hydrophilic state, or below to separate the cells from the tool, whereby a contemplated cell pattern (that is, a cell sheet having a desired shape) is rapidly recovered.

The cell pattern recovery tool according to the present invention can be used to prepare a cell pattern from various cells, for example, various in-vivo tissues, epithelial cells or endothelial cells constituting organs, contractile skeletal muscle cells, smooth muscle cells, cardiac muscle cells, neurons constituting a nerve system, glia cells, fibroblast cells, hepatic parenchymal cells, non-hepatic parenchymal cells, and adipose cells related to the metabolism of the living body, stem cells present, in various tissues, as cells having a differentiation capacity, and, further, marrow cells and ES cells. The cell pattern thus prepared has a desired specific shape. Further, adhesion factors present on the surface thereof remain intact. In addition, the part in contact with the cell culture surface has a uniform quality. Therefore, the cell pattern recovery tool can be advantageously utilized, for example, for practice of regenerative medical techniques. Further, the utilization of the cell pattern can lead to development to application to detection devices such as biosensors.

In the present specification, expression of values using "about" and "approximately" connotes a fluctuation of values that can be tolerated by a person having ordinary skill in the art in attaining the object by setting the values.

EXAMPLES

The present invention is further illustrated by the following Examples that are not intended as a limitation of the invention.

Example 1

(1-1) Preparation of Temperature Responsive Film

N-Isopropylacrylamide was dissolved in isopropyl alcohol (IPA) to give a final concentration of 20% by weight. A commercially available easy-adhesion polyethylene terephthalate film (Transparent 50-F Sepa 1090, available from SANKO SANGYO CO., LTD.) (hereinafter sometimes abbreviated to "easy-adhesion PET") was provided and cut into a 10-cm square size. The solution was developed on an easy-adhesion surface of the easy-adhesion PET and was coated by a Mayer bar on the easy-adhesion surface of the easy-adhesion PET. The surface of the sample thus obtained was irradiated with electron beams by an electron beam irradiation device (manufactured by IWASAKI ELECTRIC CO., LTD.) to graft-polymerize the solution. In this case, the exposure dose of the electron beams was 300 kGy.

(1-2) Formation of Cell Adhesion Inhibiting Material

Methacryloxysilane (TSL8370, available from Momentive Performance Materials Inc.) was provided and was then diluted with isopropyl alcohol (IPA) to a concentration of 0.1% by weight.

The film thus formed was fixed to a 0.7 mm-thick glass with a tape and was coated with methacryloxysilane by a spinner (manufactured by MIKASA Co., Ltd.) for silane treatment. In this case, methacryloxysilane was spin coated under conditions of 700 rpm×3 sec.

Separately, polyethylene glycol diacrylate (molecular weight 300, available from Aldrich) was diluted with pure water to give a final concentration of 50% by weight. 2-Hydroxy-4'-(2-hydroxyethoxy)-2-methylpropiophenone (available from Aldrich) was added as a polymerization initiator to the diluted solution to give a final concentration of 1% by weight. This solution was stirred with a stirrer for 15 min.

The solution (1 mL) was developed on the silane-treated film to form a coating which was then masked with a 150 μm-thick PET film (manufactured by Toray Industries, Inc.) so as to form a desired pattern shape. Subsequently, a photomask was set 200 μm above the masking film, followed by light irradiation with 500 mW MULTI LIGHT (manufactured by USHIO INC.) for 10 sec. The light irradiation was carried out under conditions of a wavelength of 365 nm and an illuminance of 75 mW/cm$^2$.

Thereafter, the masking film was separated, and immobilization of polyethylene glycol diacrylate on the silane-treated base material was confirmed with the naked eye.

(1-3) Cell Cultivation

The cultivation support tool thus obtained was taken off to provide a sample of 20 mm$_\phi$. A pressure-sensitive adhesive layer was exposed, and the sample was attached to the bottom of a 35-mm$_\phi$ polystyrene dish (manufactured by Becton, Dickinson and Company), and the assembly was sterilized with 70% ethanol for one hr.

Mouse fibroblast cells (available from DS Pharma Biomedical Co., Ltd.) were adjusted to 5×10$^5$ cells/cm$^2$ and were seeded within the cultivation support tool.

In this case, 5% FBS-containing DMEM (manufactured by GIBCO) was used as a medium, followed by cultivation in a $CO_2$ incubator under conditions of 37° C. and 5% $CO_2$. After 48 hr from the initiation of the cultivation, it was confirmed that cells were adhered on the pattern under a phase-difference microscope.

Subsequently, Vitrigel (manufactured by AGC TECHNO GLASS CO., LTD.) was brought into contact with the top of the cell pattern, and, in this state, the assembly was allowed to stand at room temperature for 20 min. Vitrigel was then carefully separated with a pincette. It was confirmed under a phase difference microscope that the cell pattern was recovered on Vitrigel.

Example 2

(2-1) Preparation of Temperature Responsive Film

A temperature responsive film was prepared in the same manner as in step (1-1) of Example 1.

(2-2) Formation of Cell Adhesion Inhibiting Material

Methacryloxysilane (TSL8370, available from Momentive Performance Materials Inc.) was provided and was then diluted with isopropyl alcohol (IPA) to a concentration of 0.1% by weight.

The film thus formed was fixed to a 0.7 mm-thick glass with a tape and was coated with methacryloxysilane by a spinner (manufactured by MIKASA Co., Ltd.) for silane treatment. In this case, methacryloxysilane was spin coated under conditions of 700 rpm×3 sec.

Separately, polyethylene glycol methacrylate (molecular weight 525, available from Aldrich) was diluted with pure water to give a final concentration of 50% by weight. 2-Hydroxy-4'-(2-hydroxyethoxy)-2-methylpropiophenone (available from Aldrich) was added as a polymerization initiator to the diluted solution to give a final concentration of 1% by weight. This solution was stirred with a stirrer for 15 min.

The solution (1 mL) was developed on the silane-treated film to form a coating which was then masked with a 150 μm-thick PET film (manufactured by Toray Industries, Inc.) so as to form a desired pattern shape. Subsequently, a photomask was set 200 μm above the masking film, followed by light irradiation with 250 mW MULTI LIGHT (manufactured by USHIO INC.) for 20 sec. The light irradiation was carried out under conditions of a wavelength of 365 nm and an illuminance of 38 mW/cm$^2$.

Thereafter, the masking film was separated, and immobilization of polyethylene glycol methacrylate on the silane-treated base material was confirmed with the naked eye.

(2-3) Cell Cultivation

The cultivation support tool thus obtained was taken off to provide a sample of 7.5 cm. A pressure-sensitive adhesive layer was exposed, and the sample was attached to the bottom of a 100-mm$_\phi$ polystyrene dish (manufactured by Becton, Dickinson and Company), and the assembly was sterilized with ethylene oxide gas for 2 hr.

Normal human vascular endothelial cells (available from KURABO INDUSTRIES LTD.) were adjusted to $5\times10^4$ cells/cm$^2$ and were seeded within the cultivation support tool.

In this case, 10% FBS-containing HuMedia was used as a medium, followed by cultivation in a $CO_2$ incubator under conditions of 37° C. and 5% $CO_2$. After 48 hr from the initiation of the cultivation, it was confirmed that cells were adhered on the pattern under a phase-difference microscope.

Subsequently, CellShifter (manufactured by CellSeed Inc.) was brought into contact with the top of the cell pattern, and, in this state, the assembly was allowed to stand at room temperature for 20 min. CellShifter was then carefully separated with a pincette. It was confirmed under a phase difference microscope that the cell pattern was recovered on CellShifter.

Example 3

(3-1) Preparation of Temperature Responsive Film

A temperature responsive film was prepared in the same manner as in step (1-1) of Example 1.

(3-2) Formation of Cell Adhesion Inhibiting Material

Methacryloxysilane (TSL8370, available from Momentive Performance Materials Inc.) was provided and was then diluted with isopropyl alcohol (IPA) to a concentration of 1% by weight.

The film thus formed was fixed to a 0.7 mm-thick glass with a tape and was coated with methacryloxysilane by a spinner (manufactured by MIKASA Co., Ltd.) for silane treatment. In this case, methacryloxysilane was spin coated under conditions of 1000 rpm×3 sec.

Separately, polyethylene glycol diacrylate (molecular weight 525, available from Aldrich) was diluted with IPA to give a final concentration of 50% by weight. 2-Hydroxy-4'-(2-hydroxyethoxy)-2-methylpropiophenone (available from Aldrich) was added as a polymerization initiator to the diluted solution to give a final concentration of 1% by weight. This solution was stirred with a stirrer for 15 min.

The solution (2 mL) was developed on the silane-treated film, followed by treatment with a spinner at 1000 rpm for 3 sec. Subsequently, a photomask was set 200 μm above the film, followed by light irradiation with 1 kW automatic exposure system (manufactured by Japan Science Engineering Co., Ltd.) for 20 sec.

Thereafter, immobilization of polyethylene glycol diacrylate on the silane-treated base material was confirmed with the naked eye.

Thus, the opening part width and the light shielding part width were regulated to 60 μm and 300 μm, respectively, followed by mask irradiation to prepare "sample 1" of such a line pattern that the width of the areas from which the temperature responsive polymer layer was exposed (cell adhesion areas) was 300 μm and the width of the areas where the temperature responsive polymer layer was covered with the cell adhesion inhibiting material (cell adhesion inhibiting areas) was 60 μm.

"Sample 2" of such a line pattern that the width of the cell adhesion areas and the width of the cell adhesion inhibiting areas were 60 μm and 300 μm, respectively, was prepared in the same manner as described just above.

(3-3) Cell Cultivation

The cultivation support tool thus obtained was taken off to provide a sample of 7.5 cm. A pressure-sensitive adhesive layer was exposed, and the sample was attached to the bottom of a 100-mm$_\phi$ polystyrene dish (manufactured by Becton, Dickinson and Company), and the assembly was sterilized with ethylene oxide gas for 2 hr.

Bovine vascular endothelial cells (available from Health Science Research Resources Bank) were adjusted to 67000 cells/cm$^2$ and were seeded within the cultivation support tool.

After 24 hr from the initiation of the cultivation, it was confirmed that cells were adhered on the pattern under a phase-difference microscope.

Figure 3:
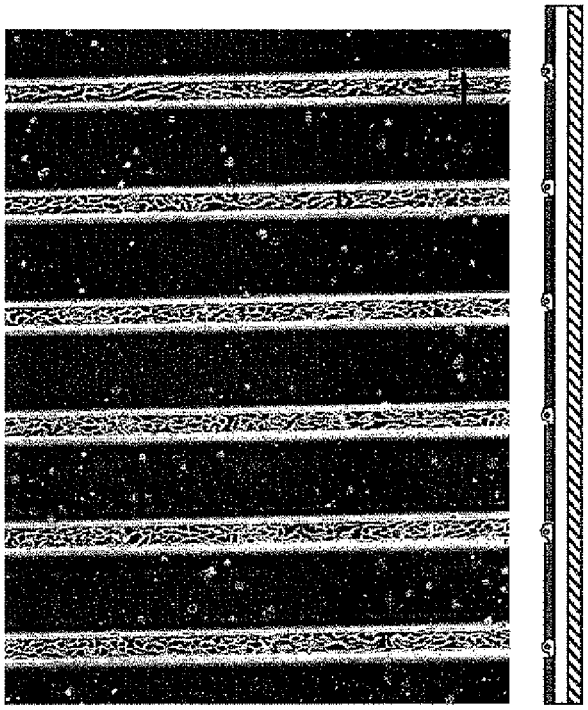
FIG. 3 is a diagram showing the results of Example 3.
Figure 3:
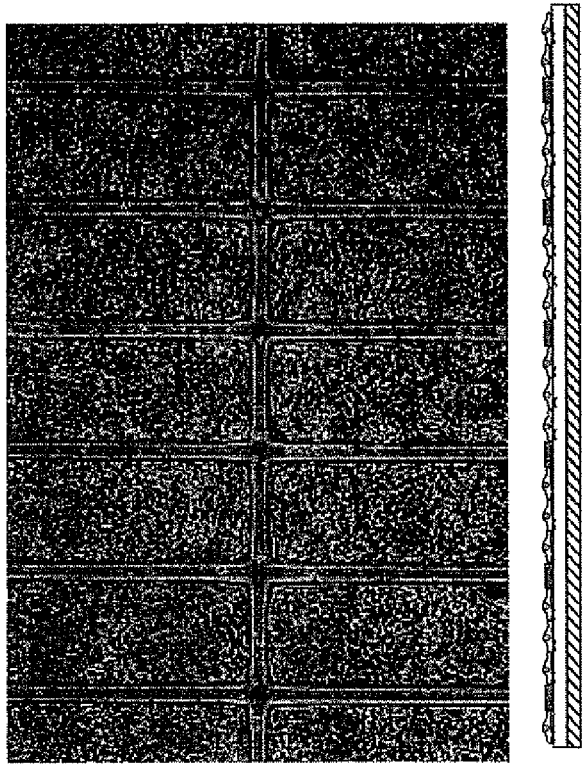

The results were as shown in FIG. 3.

FIG. 3 shows microphotographs (magnification: 40 times) of the surface of sample 1 and the surface of sample 2 after cell cultivation.

Example 4

Test on Adhesion of Polyethylene Glycol Diacrylate

A temperature responsive film was first prepared in the same manner as in step (1-1) of Example 1.

The temperature responsive film was then subjected to silane treatment in the same manner as in step (1-2) of Example 1. The opening part width and the light shielding part width were then regulated to 300 μm and 60 μm, respectively, followed by mask irradiation to prepare "sample A" of such a line pattern that the width of the areas from which the temperature responsive polymer layer was exposed (cell adhesion areas) was 60 μm and the width of the areas where the temperature responsive polymer layer was covered with the cell adhesion inhibiting material (cell adhesion inhibiting areas) was 300 μm.

"Sample B" was prepared in the same manner as described just above, except that silane treatment was not carried out.

Cell cultivation was carried out in the same manner as in Example 1, except that the samples prepared above were used. Whether the cell pattern could be properly recovered was then confirmed.

The results were as shown in Table below.

TABLE 1

| Type of sample | | Evaluation |
|---|---|---|
| Sample A | (having silane-treated temperature responsive polymer layer) | ○ |
| Sample B | (having untreated temperature responsive polymer layer) | Δ |

In the table, ○ represents that the cell pattern was properly recovered; and Δ represents that a part of polyethylene glycol diacrylate, together with the cell pattern, was disadvantageously transferred to Vitrigel.

The invention claimed is:
1. A cell pattern recovery tool comprising:
a base material layer having a surface comprising an adhesion layer;
a temperature responsive polymer layer that is provided on the base material layer and has a surface subjected to silane treatment; and
a cell adhesion inhibiting material layer provided on the temperature responsive polymer layer,
wherein, in the cell adhesion inhibiting material layer, areas where the temperature responsive polymer layer is exposed and areas where the temperature responsive polymer layer is covered with the cell adhesion inhibiting material are alternately arranged to provide a contemplated cell pattern.

2. The cell pattern recovery tool according to claim 1, wherein the width of the area which is located between the areas, where the temperature responsive polymer layer is exposed, and is covered with a cell adhesion inhibiting material is 1 μm to 500 μm.

3. The cell pattern recovery tool according to claim 1, wherein the cell adhesion inhibiting material is an ethylene glycol material.

4. The cell pattern recovery tool according to claim 1, wherein the silane treatment of the temperature responsive polymer layer has been carried out by coating the temperature responsive polymer layer with methacryloxysilane.

5. The cell pattern recovery tool according to claim 1, wherein a temperature responsive polymer constituting the temperature responsive polymer layer is poly-N-isopropylacrylamide (PIPAAm).

6. The cell pattern recovery tool according to claim 1, which further comprises a polystyrene dish provided at the bottom of the base material layer through a pressure-sensitive adhesive layer.

7. The cell pattern recovery tool according to claim 1, wherein the adhesion layer comprises an adhesion agent selected from the group consisting of a polyester, an acrylic ester, polyurethane, polyethyleneimine, a silane coupling agent, and perfluorooctanesulfonic acid.

8. The cell pattern recovery tool according to claim 1, wherein the contemplated cell pattern is a line pattern.

9. A process for producing a cell pattern recovery tool according to claim 1, the process comprising:
forming a temperature responsive polymer layer on a base material layer having a surface comprising an adhesion layer; then subjecting the surface of the temperature responsive polymer layer to silane treatment; and forming a cell adhesion inhibiting material layer, through a photopolymerization reaction on the silane-treated surface, in a shape that can form a contemplated cell pattern,
wherein, in the cell adhesion inhibiting material layer, areas where the temperature responsive polymer layer is exposed and areas where the temperature responsive polymer layer is covered with the cell adhesion inhibiting material are alternately arranged to provide a contemplated cell pattern.

10. A process for preparing a cell pattern, the process comprising: seeding cells on a cell pattern recovery tool according to claim 1, cultivating the cells under temperature conditions suitable for cultivation; then bringing the tool to a critical dissolution temperature, at which the temperature responsive polymer is converted from a hydrophobic state to a hydrophilic state, or below to separate the cells from the tool, whereby a contemplated cell pattern is rapidly recovered.

11. The process according to claim 10, wherein the critical dissolution temperature is room temperature.

* * * * *